US012778510B2

(12) United States Patent
Glenn et al.

(10) Patent No.: US 12,778,510 B2
(45) Date of Patent: Nov. 3, 2026

(54) EAR-WEARABLE ELECTRONIC DEVICE INCLUDING IN-EAR OPTICAL HEART RATE AND BLOOD OXYGEN SATURATION SENSOR

(71) Applicant: STARKEY LABORATORIES, INC., Eden Prairie, MN (US)

(72) Inventors: Janet Glenn, Minneapolis, MN (US); Peter Flanagan, Minneapolis, MN (US); Craig Feldsien, Eden Prairie, MN (US); Kyle Olson, St. Louis Park, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 675 days.

(21) Appl. No.: 17/971,824

(22) Filed: Oct. 24, 2022

(65) Prior Publication Data

US 2023/0130889 A1 Apr. 27, 2023

Related U.S. Application Data

(60) Provisional application No. 63/271,375, filed on Oct. 25, 2021.

(51) Int. Cl.
*A61B 5/00* (2006.01)
*A61B 5/0205* (2006.01)
(Continued)

(52) U.S. Cl.
CPC .......... *A61B 5/6843* (2013.01); *A61B 5/0205* (2013.01); *A61B 5/14551* (2013.01);
(Continued)

(58) Field of Classification Search
CPC . A61B 5/6843; A61B 5/6817; A61B 5/02427; A61B 5/02438; A61B 5/02416; A61B 5/14552
See application file for complete search history.

(56) References Cited

U.S. PATENT DOCUMENTS 6,283,915 B1 9/2001 Aceti
9,820,062 B2 * 11/2017 Stewart ................ H04R 25/654
(Continued)

FOREIGN PATENT DOCUMENTS

WO WO-2014116942 A2 * 7/2014 ............. A61B 5/681
WO WO-2017183027 A1 * 10/2017 ........... A61B 5/0004
WO 2021/022063 2/2021

OTHER PUBLICATIONS

Parris, Chad and Feldsien, Craig, “The Dash Pro Tailored by Starkey Hearing Technologies”, Starkey Hearing Technologies, 3 pages, 2017.

*Primary Examiner* — Sean P Dougherty
(74) *Attorney, Agent, or Firm* — Mueting Raasch Group

(57) ABSTRACT

An ear-wearable electronic device comprises a shell having a uniquely-shaped outer surface that corresponds uniquely to an ear geometry of a wearer of the device. The shell comprises a window through a proximal portion of the shell and positioned at ear canal tissue when the device is deployed in the wearer’s ear. An optical sensor, such as a photoplethysmograph (PPG) sensor, is disposed in the window. A biasing member has a uniquely-shaped outer surface that corresponds uniquely to a geometry of at least a portion of a pinna of the wearer’s ear. The biasing member is configured to generate a biasing force sufficient to maintain static positioning of the optical sensor relative to the ear canal tissue during wearer body and jaw movement.

23 Claims, 6 Drawing Sheets

(51) Int. Cl.
*A61B 5/024* (2006.01)
*A61B 5/1455* (2006.01)

(52) U.S. Cl.
CPC ........ *A61B 5/6817* (2013.01); *A61B 5/02427* (2013.01); *A61B 5/02438* (2013.01); *A61B 2562/185* (2013.01)

(56) References Cited

U.S. PATENT DOCUMENTS

| | | | | |
|---|---|---|---|---|
| 10,834,483 | B2 * | 11/2020 | Aumer | A61B 5/6802 |
| 10,873,798 | B1 * | 12/2020 | Jackson | G06F 3/017 |
| 11,134,351 | B1 * | 9/2021 | Lunner | A61B 5/02125 |
| 2005/0033131 | A1 * | 2/2005 | Chen | A61B 5/14552 600/344 |
| 2008/0146890 | A1 * | 6/2008 | LeBoeuf | A61B 5/4839 600/300 |
| 2008/0253583 | A1 * | 10/2008 | Goldstein | H04R 3/04 381/92 |
| 2009/0112071 | A1 * | 4/2009 | LeBoeuf | A61B 5/0261 600/301 |
| 2010/0217099 | A1 * | 8/2010 | LeBoeuf | A61B 5/0205 600/301 |
| 2011/0091058 | A1 * | 4/2011 | Sacha | G06F 3/017 381/328 |
| 2011/0125063 | A1 * | 5/2011 | Shalon | A61B 5/4205 600/590 |
| 2016/0030809 | A1 * | 2/2016 | Wisbey | A61B 5/6817 600/301 |
| 2016/0249133 | A1 * | 8/2016 | Sørensen | A61B 5/6817 |
| 2017/0155985 | A1 | 6/2017 | Boesen | |
| 2017/0289670 | A1 * | 10/2017 | Gilbertson | H04R 1/1016 |
| 2020/0186903 | A1 * | 6/2020 | Higgins | H04R 25/65 |
| 2020/0196073 | A1 * | 6/2020 | Nielsen | H04R 25/652 |
| 2020/0196914 | A1 * | 6/2020 | Sacha | G08B 21/0446 |
| 2020/0202839 | A1 * | 6/2020 | Asada | H04R 1/105 |
| 2020/0268265 | A1 * | 8/2020 | Walsh | A61B 5/6803 |
| 2021/0069490 | A1 * | 3/2021 | Hanson | H04R 1/1058 |
| 2022/0408175 | A1 * | 12/2022 | Barnacka | A61B 8/12 |

* cited by examiner

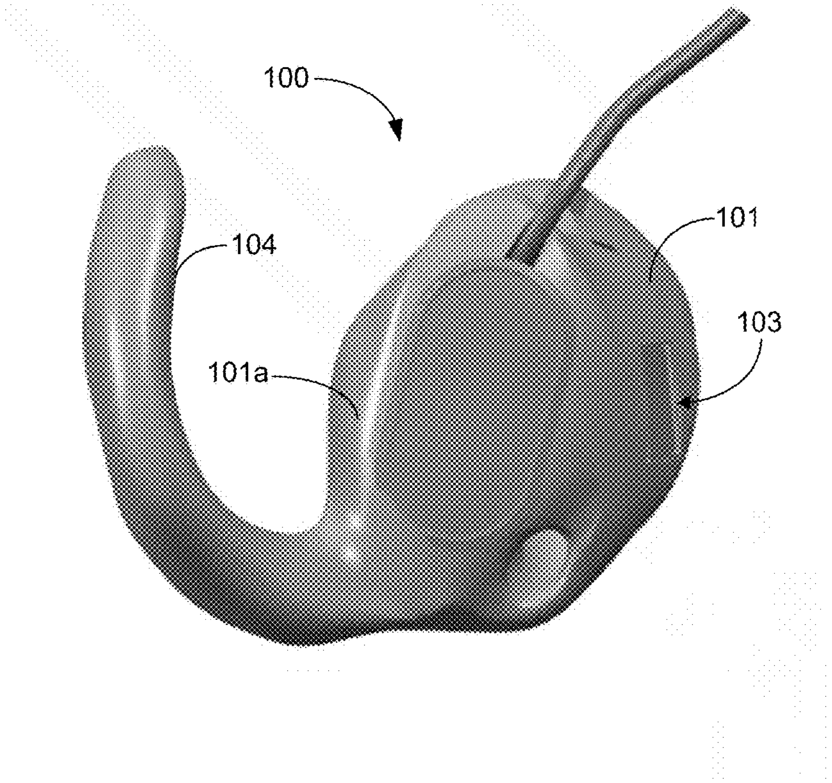
FIGURE 3
FIGURE 4
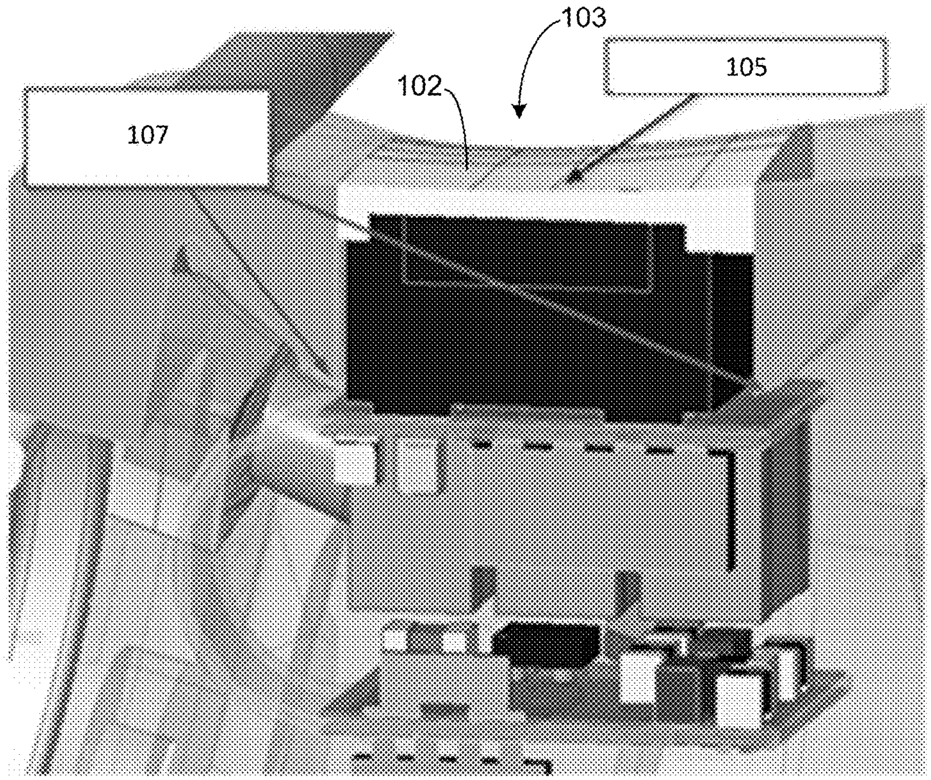

*FIGURE 9*
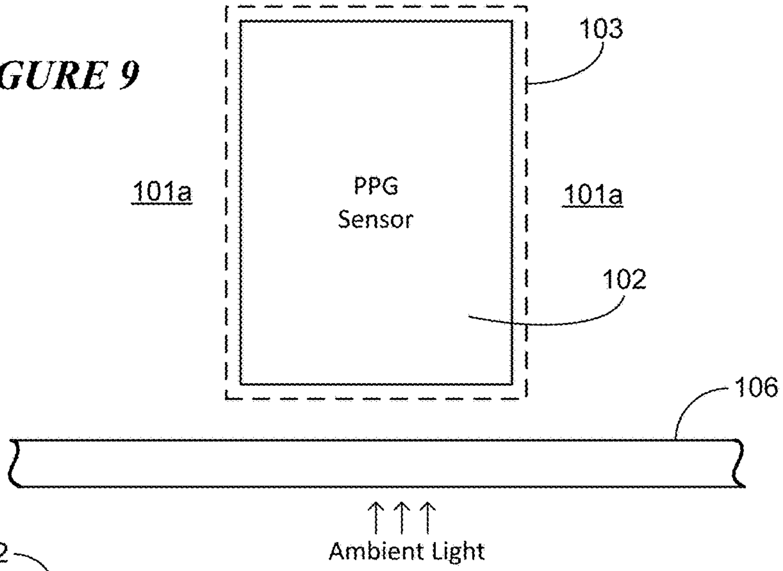
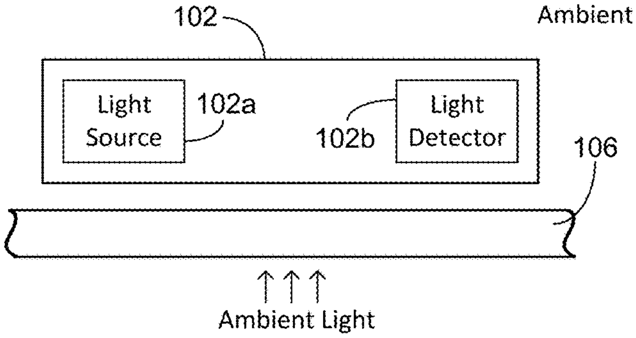
*FIGURE 10*
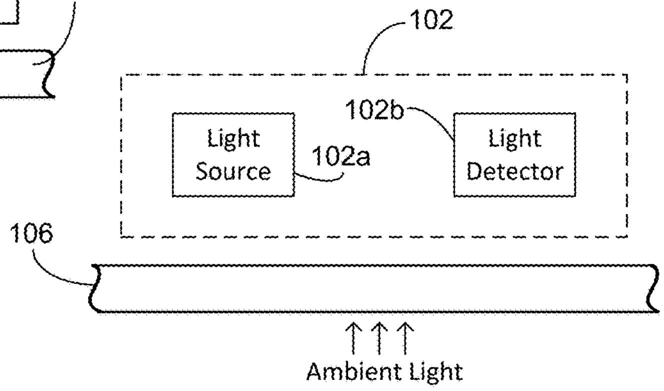
*FIGURE 11*
*FIGURE 12*
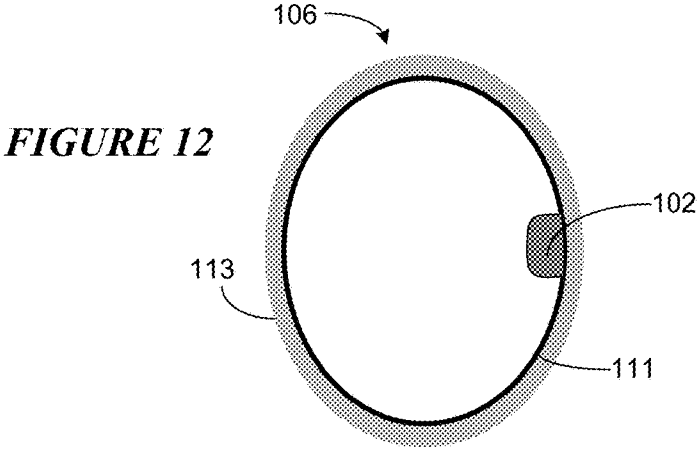

EAR-WEARABLE ELECTRONIC DEVICE INCLUDING IN-EAR OPTICAL HEART RATE AND BLOOD OXYGEN SATURATION SENSOR

RELATED APPLICATION

This application claims the benefit of U.S. Provisional Application No. 63/271,375 filed on Oct. 25, 2021, which is incorporated herein by reference in its entirety.

TECHNICAL FIELD

This application relates generally to devices and sensing methods for measuring heart rate and blood oxygen saturation from within an ear, such devices including ear-wearable electronic devices, hearing aids, commercial hearables, earbuds, personal amplification devices, and physiologic/biometric monitoring devices.

SUMMARY

Embodiments are directed to an ear-wearable electronic device comprising a shell having a uniquely-shaped outer surface that corresponds uniquely to an ear geometry of a wearer of the device. The shell comprises a window through a proximal portion of the shell and positioned against ear canal tissue when the device is deployed in the wearer's ear. An optical sensor, such as a photoplethysmograph (PPG) sensor, is disposed in the window. A biasing member has a uniquely-shaped outer surface that corresponds uniquely to a geometry of at least a portion of a pinna of the wearer's ear. The biasing member is configured to generate a biasing force sufficient to maintain static positioning of the optical sensor relative to the ear canal tissue during wearer body and jaw movement.

Embodiments are directed to a method implemented by an ear-wearable electronic device deployed in an ear of a wearer comprising generating, using a biasing member of the device, an apposition force sufficient to maintain static positioning of an optical sensor of the device relative to tissue of the wearer's ear canal during wearer body and jaw movement. The method also comprises producing sensor signals by the optical sensor positioned within a window of a shell of the device, the shell having a uniquely-shaped outer surface that corresponds uniquely to an ear geometry of the wearer. The method further comprises calculating, using a processor of the device, one or both of heart rate and blood oxygen saturation (SpO2) of the wearer using the sensor signals.

Embodiments are directed to an ear-wearable electronic device comprising a shell having a uniquely-shaped outer surface that corresponds uniquely to an ear geometry of a wearer of the device, the shell comprising a window through a proximal portion of the shell and positioned at ear canal tissue when the device is deployed in the wearer's ear. An optical sensor is disposed in the window. A biasing member has a uniquely-shaped outer surface that corresponds uniquely to a geometry of at least a portion of a pinna of the wearer's ear. The biasing member is configured to generate a biasing force sufficient to maintain static positioning of the optical sensor relative to the ear canal tissue during wearer body and jaw movement.

Embodiments are directed to a method implemented by an ear-wearable electronic device deployed in an ear of a wearer comprising generating, using a biasing member of the device, an apposition force sufficient to maintain static positioning of an optical sensor of the device relative to canal tissue of the wearer's ear during wearer body and jaw movement. The method also comprises producing sensor signals by the optical sensor positioned within a window of a shell of the device, the shell having a uniquely-shaped outer surface that corresponds uniquely to an ear geometry of the wearer. The method further comprises calculating, using a processor of the device, one or both of heart rate and blood oxygen saturation (SpO2) of the wearer using the sensor signals.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein:

FIGS. 3-8 illustrate features of an ear-wearable electronic device which incorporates a PPG sensor in accordance with any of the embodiments disclosed herein;

FIG. 9 illustrates a PPG sensor positioned within a window of the shell body and an optical seal arrangement configured to inhibit ambient light from reaching the PPG sensor when the device is deployed in the wearer's ear in accordance with any of the embodiments disclosed herein;

FIG. 10 illustrates an integrated circuit PPG sensor positioned relative to an optical seal arrangement configured to inhibit ambient light from reaching the PPG sensor when the device is deployed in the wearer's ear in accordance with any of the embodiments disclosed herein;

FIG. 11 illustrates a PPG sensor comprising discrete light source and light detector components positioned relative to an optical seal arrangement configured to inhibit ambient light from reaching the PPG sensor when the device is deployed in the wearer's ear in accordance with any of the embodiments disclosed herein;

FIG. 12 illustrates a seal arrangement defined by an overbuild region of the shell body in accordance with any of the embodiments disclosed herein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1A:
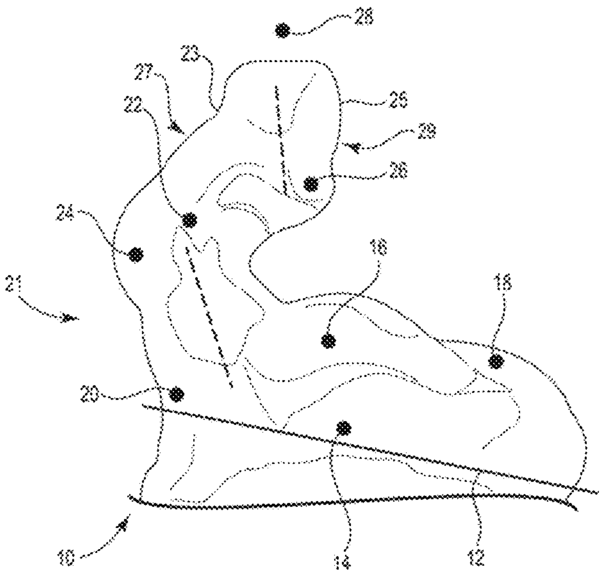
FIG. 1A is an illustration of a person's ear including various anatomical features.

Embodiments of the disclosure are directed to an ear-wearable electronic device which includes an optical sensor (e.g., a PPG sensor) and a biasing member configured to produce an apposition force sufficient to maintain stationary positioning of the PPG sensor against ear canal tissue when the device is deployed in a wearer's ear. Embodiments are directed to a custom hearing device shell that supports a PPG sensor and provides for continuous contact and pressure between the PPG sensor and ear canal tissue via a biasing member arrangement.

Embodiments are directed to an ear-wearable electronic device comprising a custom shell having a uniquely-shaped outer surface (e.g., organic surface) that corresponds uniquely to the ear geometry of a wearer of the device. The custom shell supports at least one PPG sensor at a location within the ear canal that has access to underlying blood vessels. It has been found that the tragal wall provides good and consistent access to underlying arterial vasculature, and that positioning the PPG sensor at a tragal wall location provides good and consistent PPG sensor signals needed for calculating the wearer's heart rate and/or blood oxygen saturation (SpO2). It is understood that the PPG sensor can be located relative to ear canal tissue other than that at the tragal wall. For example, the PPG sensor can be positioned at a concha-facing position or an anti-tragus-facing location for accessing the posterior auricular artery. By way of further example, the PPG sensor can be positioned at the tragal-notch region.

During development of one representative device, it was found that providing continuous contact between the PPG sensor and ear canal tissue was sufficient to obtain accurate heart rate measurements, but insufficient to obtain accurate and consistent SpO2 measurements. To address this inadequacy, a shell of this representative device was developed that provides for the application of a constant pressure by the PPG sensor against the tragal wall in response to a biasing (apposition) force generated by a biasing member extending from the shell body. In some implementations, a seal arrangement developed on the shell body proximal of the PPG sensor produces additional pressure that physically forces the shell into the ear canal. In such implementations, the biasing member and the seal arrangement can be configured to cooperate as a canal lock for retaining the device in the wearer's ear during body and jaw movement. In other implementations, a canal lock may be excluded.

The custom shell of the representative device includes a biasing member that extends from the body of the shell and has a uniquely-shaped outer surface (e.g., organic surface) that corresponds uniquely to a geometry of at least a portion of the wearer's pinna (e.g., antitragus and/or antihelix). The biasing member is configured to generate a specified biasing force sufficient to maintain static positioning of the optical sensor relative to the tragal wall during wearer body and jaw movement. The specified biasing force allows for accurate sensing of the wearer's blood oxygen saturation (SpO2) in addition to heart rate. It was found that a specified amount of apposition force between the PPG sensor and ear canal tissue (discussed below) is needed to obtain consistently accurate SpO2 measurements, in additional to accurate heart rate measurements. In some implementations, it is desirable to position the PPG sensor on a flat (e.g., the flattest) part of the tragal wall close to the first bend as is feasible (e.g., away from the face plate in the first bend direction).

According to various implementations, a seal arrangement is provided that serves as an optical seal as well as an acoustic seal. As will be described below, the seal arrangement can be implemented using overbuild material to provide a custom optical/acoustic seal. The overbuild material provides for a seal arrangement that is modestly oversized relative to the organic size of the shell in the seal region. This intentional oversizing of the shell in the seal region serves to create additional pressure in the ear canal which physically pushes the shell into the ear canal at canal tissue location (e.g., the tragal wall), so that the PPG sensor is always in contact, with pressure applied, to tissue of the ear canal. The seal arrangement provides supplemental pressure that cooperates with the biasing member to generate force/pressure sufficient to maintain static positioning of the PPG sensor relative to the ear canal tissue (e.g., the tragal wall) during wearer movement (e.g., body movement, jaw movement). The combination of the biasing member and seal arrangement provides for an effective canal lock mechanism that provides stable and specific pressure between the PPG sensor and ear canal tissue during wearer movement. For example, the pressure between the PPG sensor and ear canal tissue should not exceed pressure that would crush or constrict the underlying blood vessels of the ear canal tissue, while being sufficient to maintain static positioning of the PPG sensor relative to the ear canal tissue (e.g., at the tragal wall) during wearer body and jaw movement.

Embodiments of the disclosure are defined in the claims. However, below there is provided a non-exhaustive listing of non-limiting examples. Any one or more of the features of these examples may be combined with any one or more features of another example, embodiment, or aspect described herein.

Example Ex1. An ear-wearable electronic device comprises a shell having a uniquely-shaped outer surface that corresponds uniquely to an ear geometry of a wearer of the device, the shell comprising a window through a proximal portion of the shell and positioned at a tragal wall when the device is deployed in the wearer's ear. An optical sensor is disposed in the window. A biasing member has a uniquely-shaped outer surface that corresponds uniquely to a geometry of at least a portion of a pinna of the wearer's ear, the biasing member configured to generate a biasing force sufficient to maintain static positioning of the optical sensor relative to the tragal wall during wearer body and jaw movement.

Example Ex2. The device according to Ex1, wherein the optical sensor is configured to apply a constant pressure against the tragal wall in response to the biasing force generated by the biasing member.

Example Ex3. The device according to Ex1, wherein the biasing member has a uniquely-shaped outer surface that corresponds uniquely to a geometry of at least a portion of one or both of an antitragus and an antihelix of the wearer's ear.

Example Ex4. The device according to Ex1, wherein the biasing member is configured to generate an apposition force sufficient to retain the device in the ear during wearer body and jaw movement.

Example Ex5. The device according to Ex1 or Ex4, wherein the biasing member is configured to generate an apposition force sufficient to prevent air gaps between the optical sensor and the tragal wall during wearer body and jaw movement.

Example Ex6. The device according to one or more of Ex1 to Ex5, wherein the biasing member comprises an overbuild of material covering the portion of the biasing member surface configured to contact one or both of an antitragus and an antihelix of the wearer's ear.

Example Ex7. The device according to Ex6, wherein the overbuild of material comprises an increase of material on the outer surface of the biasing member of about 5 to 20 percent.

Example Ex8. The device according to one or more of Ex1 to Ex7, wherein the window is positioned at a flat region of the tragal wall proximate a first bend of the wearer's ear when the device is deployed in the wearer's ear.

Example Ex9. The device according to one or more of Ex1 to Ex8, wherein the window is positioned at a region of the tragal wall adjacent an anterior auricular artery of an external carotid artery when the device is deployed in the wearer's ear.

Example Ex10. The device according to one or more of Ex1 to Ex9, comprising a seal arrangement configured to inhibit ambient light from reaching the optical sensor when the device is deployed in the wearer's ear.

Example Ex11. The device according to Ex10, wherein the seal arrangement is configured to inhibit ambient sound from reaching the wearer's ear drum when the device is deployed in the wearer's ear.

Example Ex12. The device according to Ex10 or Ex11, wherein the seal arrangement comprises an overbuild of material at a portion of the shell proximal of the optical sensor in an outer ear direction.

Example Ex13. The device according to Ex12, wherein the overbuild of shell material comprises an increase of material at the proximal portion of the shell of about 5 to 20 percent.

Example Ex14. The device according to Ex12 or Ex13, wherein the overbuild of material produces pressure that physically pushes the shell into the wearer's ear canal when the device is deployed in the wearer's ear.

Example Ex15. The device according to one or more of Ex10 to Ex14, wherein the biasing member and the seal arrangement are configured to cooperate as a canal lock for retaining the device in the wearer's ear.

Example Ex16. The device according to one or more of Ex1 to Ex15, wherein the optical sensor is configured to detect or produce signals indicative of heart rate.

Example Ex17. The device according to one or more of Ex1 to Ex16, wherein the optical sensor is configured to produce signals indicative of blood oxygen saturation (SpO2).

Example Ex18. The device according to one or more of Ex1 to Ex17, wherein the optical sensor comprises a photoplethysmograph (PPG) sensor.

Example Ex19. The device according to one or more of Ex1 to Ex18, comprising an optical lens covering the optical sensor and configured to contact the tragal wall when the device is deployed in the wearer's ear.

Example Ex20. The device according to one or more of Ex1 to Ex19, wherein the optical sensor comprises an integrated circuit package comprising a light source and a light detector.

Example Ex21. The device according to one or more of Ex1 to Ex19, wherein the optical sensor comprises a discrete light source spaced apart from a discrete light detector.

Example Ex22. The device according to one or more of Ex1 to Ex21, wherein the device defines a MC, ITE, ITC, CIC or IIC type hearing device.

Example Ex23. A method implemented by an ear-wearable electronic device deployed in an ear of a wearer comprises generating, using a biasing member of the device, an apposition force sufficient to maintain static positioning of an optical sensor of the device relative to a tragal wall of the wearer's ear during wearer body and jaw movement, producing sensor signals by the optical sensor positioned within a window of a shell of the device, the shell having a uniquely-shaped outer surface that corresponds uniquely to an ear geometry of the wearer, and calculating, using a processor of the device, one or both of heart rate and blood oxygen saturation (SpO2) of the wearer using the sensor signals.

Example Ex24. The method according to Ex23, comprising inhibiting light from reaching the optical sensor.

Example Ex25. The method according to Ex23 or Ex24, comprising inhibiting ambient sound from passing around the device and reaching the wearer's ear drum;

Example Ex26. The method according to one or more of Ex23 to Ex25, comprising causing the optical sensor to maintain constant pressure against the tragal wall in response to the apposition force.

Example Ex27. The method according to one or more of Ex23 to Ex26, comprising inhibiting light from reaching the optical sensor and inhibiting ambient sound from passing around the device and reaching the wearer's ear drum using a seal arrangement defined by an overbuild region of the shell, and retaining the device in the wearer's ear via the biasing member and the seal arrangement cooperating as a canal lock.

Example Ex28. An ear-wearable electronic device comprises a shell having a uniquely-shaped outer surface that corresponds uniquely to an ear geometry of a wearer of the device. The shell comprises a window through a proximal portion of the shell and is positioned at ear canal tissue when the device is deployed in the wearer's ear. An optical sensor is disposed in the window. A biasing member has a uniquely-shaped outer surface that corresponds uniquely to a geometry of at least a portion of a pinna of the wearer's ear, and is configured to generate a biasing force sufficient to maintain static positioning of the optical sensor relative to the ear canal tissue during wearer body and jaw movement.

Example Ex29. The device according to Ex28, wherein the optical sensor is positioned at a concha-facing location.

Example Ex30. The device according to Ex28, wherein the optical sensor is positioned at an anti-tragus-facing location.

Example Ex31. The device according to Ex28, wherein the optical sensor is positioned at a tragal-notch region.

Example Ex32. A method implemented by an ear-wearable electronic device deployed in an ear of a wearer comprises generating, using a biasing member of the device, an apposition force sufficient to maintain static positioning of an optical sensor of the device relative to canal tissue of the wearer's ear during wearer body and jaw movement, producing sensor signals by the optical sensor positioned within a window of a shell of the device, the shell having a uniquely-shaped outer surface that corresponds uniquely to an ear geometry of the wearer, and calculating, using a processor of the device, one or both of heart rate and blood oxygen saturation (SpO2) of the wearer using the sensor signals.

Example Ex33. The method according to Ex32, wherein the optical sensor is positioned at a concha-facing location.

Example Ex34. The method according to Ex32, wherein the optical sensor is positioned at an anti-tragus-facing location.

Example Ex35. The method according to Ex32, wherein the optical sensor is positioned at a tragal-notch region.

Figure 1B:
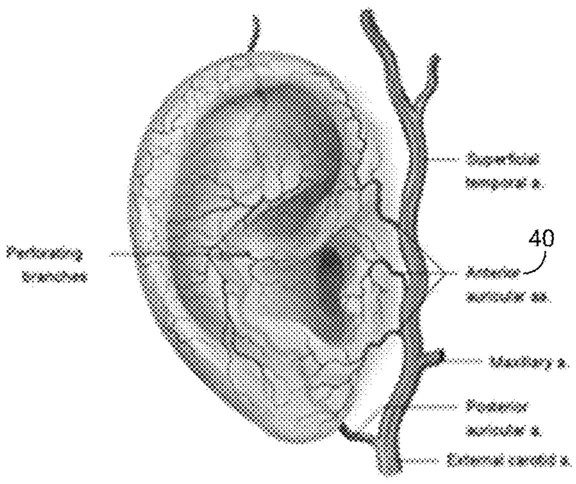
FIG. 1B shows vasculature of the ear, including the anterior auricular arteries which are accessible from the tragal wall region of the ear canal.

FIG. 1A is an illustration of a person's ear 10 and, in particular, the ear canal 22. The ear 10 illustrated in FIG. 1A shows a number of anatomical features near the ear line 12, including the antitragus 14, concha 16, helix 18, and tragus 20. The ear canal 22 includes a proximal section 21 between the tragus 20 and a first bend 24 of the canal 22. A middle section 27 is shown between the first bend 24 and a second bend 26 of the canal 22. A distal section 29 is shown between the second bend 26 and a tympanic membrane (ear drum) 28. FIG. 1B shows vasculature of the ear, including the anterior auricular arteries 40 which are accessible from the tragal wall region 20 of the ear canal 22. As discussed previously, other vasculature of the ear (e.g., posterior auricular artery) can be accessed by appropriate placement of the optical sensor (e.g., a PPG sensor at a concha-facing position or an anti-tragus-facing location).

Figure 1C:
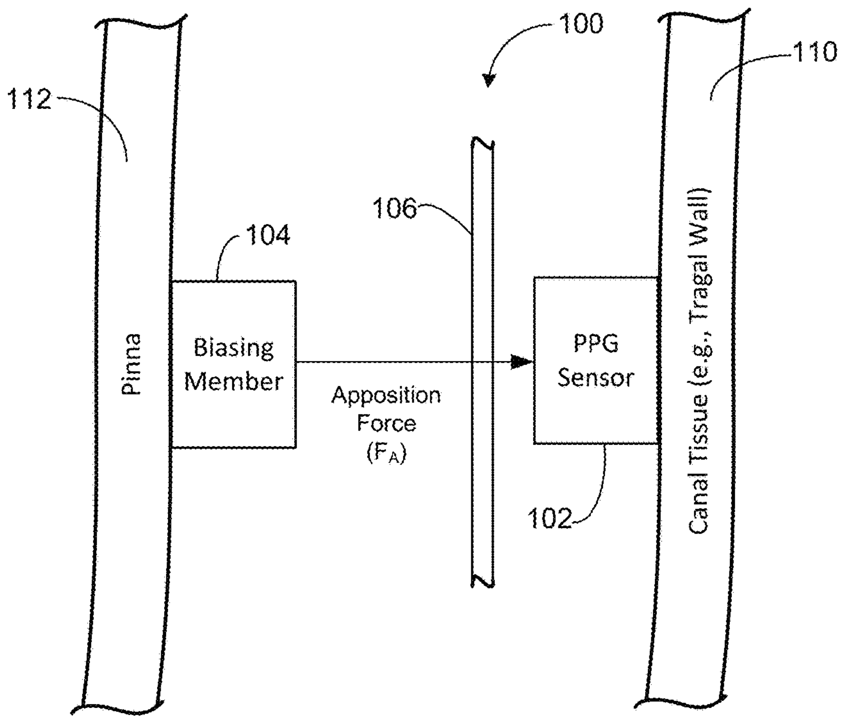
FIG. 1C illustrates an ear-wearable electronic device in accordance with any of the embodiments disclosed herein.

FIG. 1C illustrates an ear-wearable electronic device in accordance with any of the embodiments disclosed herein. The ear-wearable electronic device 100 includes a shell (not shown, but see FIG. 3 for example) which supports an optical sensor 102. The optical sensor 102 is preferably configured as a PPG sensor. The PPG sensor 102 is situated on the shell such that the PPG sensor 102 is positioned relative to tissue of the ear canal. More particularly, the PPG sensor is situated within a window (e.g., a cut-out) of the shell such that the PPG sensor 102 is positioned at a tragal wall of the ear canal (see FIG. 1A) when the device 100 is deployed in the wearer's ear. The PPG sensor 102 is configured to produce sensor signals which can be used by a processor of the device 100 to compute various physiologic data including, for example, heart rate and blood oxygen saturation (SpO2).

The ear-wearable electronic device 100 includes a biasing member 104 configured to fit within and against a portion of a pinna of the wearer's ear. In general, the biasing member 104 is shaped to fit within a portion of the pinna such that the biasing member 104 generates an apposition force, FA, sufficient to maintain static positioning of the PPG sensor 102 relative to the tragal wall during wearer movement. For example, the biasing member 104 generates an apposition force, FA, sufficient to retain the ear-wearable electronic device 100 in the ear during wearer movement. Such movements includes head and jaw movement (e.g., chewing, talking, sitting, walking, jogging). According to any of the embodiments disclosed herein, the biasing member 104 is shaped to fit within and against at least a portion of an antitragus and/or an antihelix of the wearer's ear (see FIG. 1A). In this regard, the biasing member 104 serves as a canal lock that generates a specified amount of apposition force sufficient to securely retain the ear-wearable electronic device 100 in the ear and to take accurate physiologic readings (e.g., heart rate, SpO2) from within the ear canal.

The ear-wearable electronic device 100 includes a seal arrangement 106 configured to inhibit ambient light from reaching the PPG sensor 102 when the device 100 is deployed in the wearer's ear. In some implementations, the seal arrangement 106 is an optical seal arrangement. In other implementations, the seal arrangement 106 is configured as both an optical seal and an acoustic seal, such that the acoustic seal is configured to inhibit ambient sound from reaching the wearer's eardrum when the device is deployed in the wearer's ear.

Figure 2:
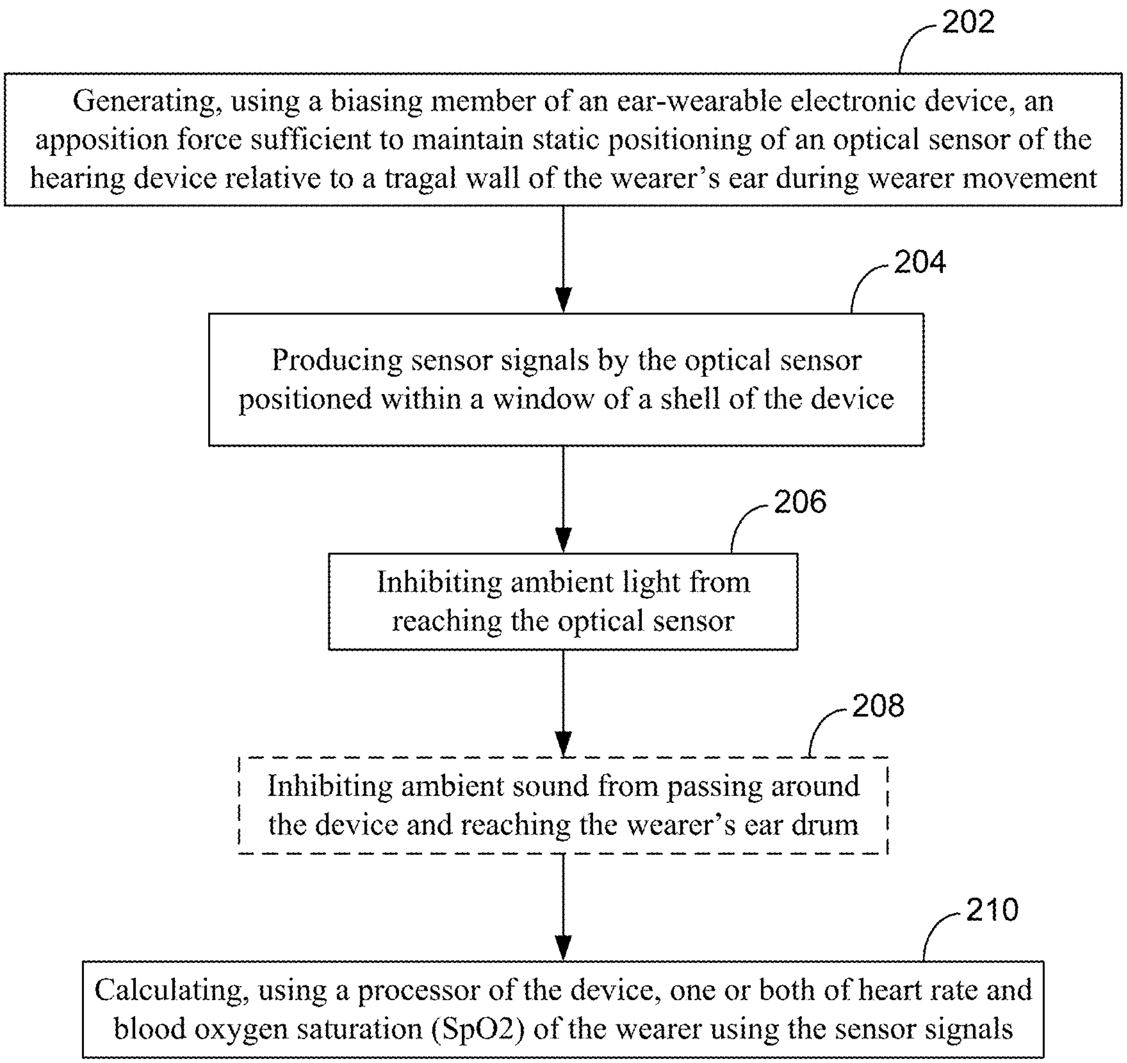
FIG. 2 illustrates a method implemented by the ear-wearable electronic device shown in FIG. 1C in accordance with any of the embodiments disclosed herein.
Figure 5:
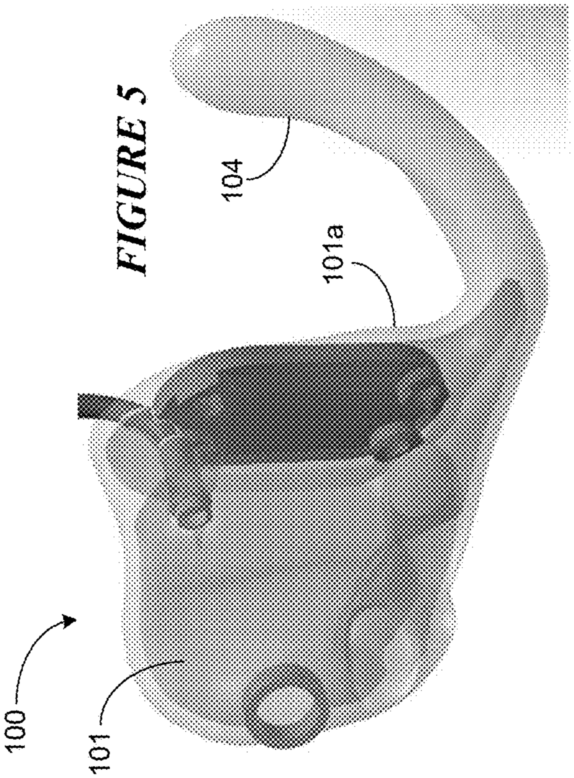
Figure 6:
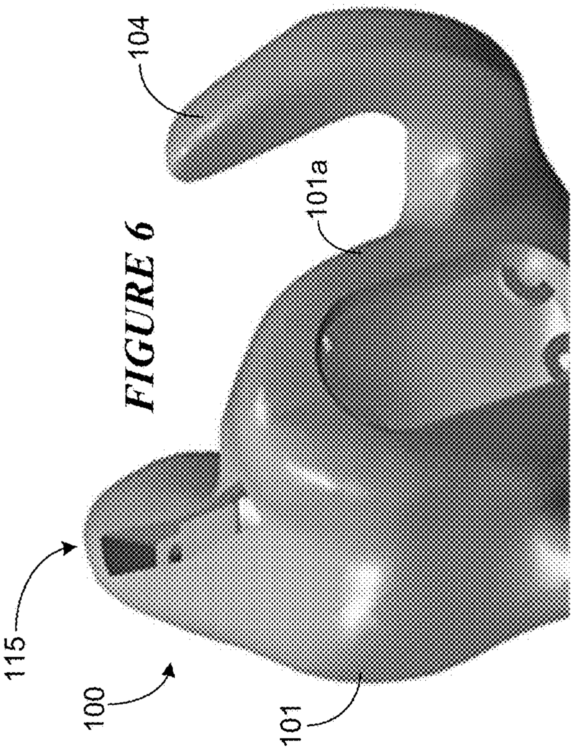
Figure 7:
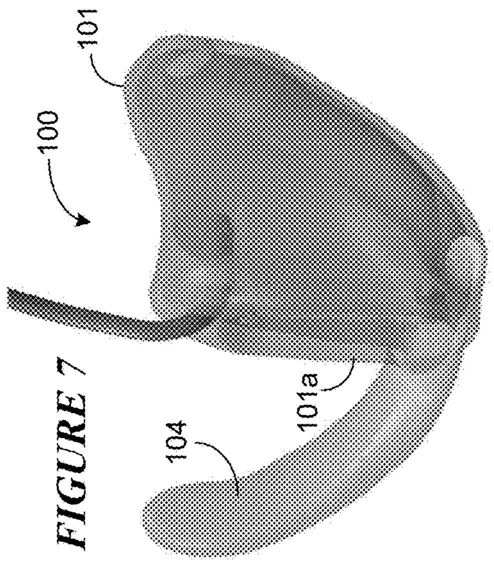
Figure 8:
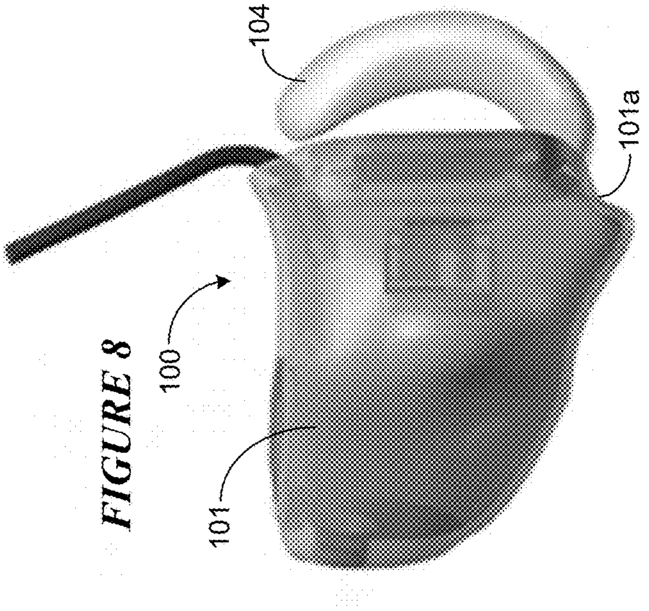

FIG. 2 illustrates a method implemented by the ear-wearable electronic device 100 shown in FIG. 1C. The method shown in FIG. 2 involves generating 202, using a bias member of the ear-wearable electronic device, an apposition force sufficient to maintain static positioning of an optical sensor of the device relative to a tragal wall of the wearer's ear during wearer movement. The method involves producing 200 sensor signals by the optical sensor positioned within a window of a shell of the ear-wearable electronic device. The method can also involve inhibiting 206 ambient light from reaching the optical sensor. In some implementations, inhibiting 206 ambient light from reaching the optical sensor also involves inhibiting 208 ambient sound from passing around the device and reaching the wearer's eardrum. The method further involves calculating 210, using a processor of the ear-wearable device 100, one or both of heart rate and blood oxygen saturation (SpO2) of the wearer using the sensor signals.

FIGS. 3-8 illustrate features of an ear-wearable electronic device 100 which incorporates a PPG sensor 102 in accordance with any of the embodiments disclosed herein. FIGS. 3 and 5-8 illustrate different views of the device 100. FIG. 4 is a zoomed-in view of the device 100 illustrating various details of the PPG sensor 102.

As is best seen in FIG. 3, the ear-wearable electronic device 100 includes a shell 101 having a uniquely-shaped outer surface that corresponds uniquely to an ear geometry of a wearer of the device 100. The unique shape of the outer surface of the shell 101 can be based on a mold impression (e.g., impression negative) of the wearer's ear. The shell 101 includes a window 103 through a proximal portion of the shell 101. The window 103 is preferably positioned at a tragal wall of the wearer's ear canal when the device 100 is deployed in the wearer's ear.

As can be seen in FIG. 4, an optical sensor, such as a PPG sensor 102, is disposed in the window 103. The PPG sensor 102 can be potted with a suitable resin 105. In some implementations, the PPG sensor 102 includes an optical lens configured to contact the tragal wall when the device 100 is deployed in the wearer's ear. The shell body 101*a* can include structures 107, such as pyramid shell structures, that provide depth control of the PPG sensor 102 when the PPG sensor 102 is installed in the shell body 101*a*.

The PPG sensor 102 is preferably placed against the tragal wall as deep into the ear canal as possible. The possible depth of the PPG sensor 102 is defined by the wearer's unique ear anatomy and wearer comfort, as well as internal shell features. The objective of PPG sensor placement is to take advantage of the larger of the anterior auricular arteries 40 (see FIG. 1B) so that the PPG sensor 102 can detect blood flow. These arteries are located in the muscle which lies on top of the temporal bone. As such, the window 103 within which the PPG sensor 102 is situated, is positioned at a region of the tragal wall adjacent anterior auricular arteries of an external carotid artery when the device 100 is deployed in the wearer's ear.

Extending from the shell body 101*a* is a biasing member 104 having a uniquely-shaped outer surface that corresponds uniquely to a geometry of at least a portion of the pinna of the wearer's ear. The unique shape of the outer surface of the biasing member 104 can be based on a mold impression of the wearer's pinna. For example, the outer surface of the biasing member 104 can be based on a mold impression (e.g., impression negative) of the wearer's antitragus, antihelix or both the antitragus and antihelix of the wearer's pinna. In other implementations, the biasing force can be produced without provision of the biasing member 104, such as from an overbuild region of the shell body 101*a* that defines a seal region (e.g., acoustic seal, light seal, acoustic/light seal), as discussed below.

The biasing member 104 is configured to generate a biasing force, FA, sufficient to maintain static positioning of the PPG sensor 102 relative to the tragal wall during wearer movement. In some implementations, the biasing member has a uniquely-shaped outer surface that corresponds uniquely to a geometry of at least a portion of the antitragus and/or an antihelix of the wearer's ear. As was discussed previously, the biasing member 104 is configured to generate an apposition force, FA, sufficient to retain the shell body 101*a* in the ear during wearer movement.

The biasing member 104 includes overbuild regions at portions that contact the antitragus and/or antihelix of the wearer's ear. These overbuild regions result in the production of additional force at the antitragus and/or antihelix of the wearer's ear when the device 100 is fully deployed in the wearer's ear. The term overbuild refers to the additive manufacturing process of adding material over the unique impression negative of a wearer's ear (e.g., via wax offset/dipping hand-pouring). This additional material creates regions of additional force produced by the overbuild at specified locations of the biasing member 104.

According to various implementations, the biasing member 104 is configured to provide consistent pressure at the PPG sensor location of the shell body 101*a*. This pressure must be sufficiently high to ensure that static positioning of the PPG sensor 102 relative to the tragal wall is maintained during wearer movement, while also allowing for measurement of physiologic parameters that rely on blood pressure. The biasing member 104, for example, can be configured to generate an apposition force, FA, of between about 15 and 45 mmHG (e.g., —30 mmHG), considering that a low diastolic blood pressure is less than about 60 mmHG.

During device development, it was found that air gaps between the PPG sensor 102 and tissue of the ear canal resulted in disruption of the algorithm that computes various physiologic parameters or conditions of the wearer (e.g., heart rate, SpO2), and caused errors in such computations. Referring now to FIG. 9, the PPG sensor 102 is shown positioned within a window 103 of the shell body 101*a*. The shell body 101*a* includes an optical seal arrangement 106 configured to inhibit ambient light from reaching the PPG sensor 102 when the device 100 is deployed in the wearer's ear. The optical seal arrangement 106 is preferably defined by an overbuild region of the shell body 101*a*. For example, and with reference to FIG. 12, the optical seal arrangement 106 includes an overbuild region 113 of the shell body 101*a* positioned proximal of the PPG sensor 102 in the outer ear direction. At this location, the overbuild region 113 is positioned at or near the canal entrance before the first bend when the device 100 is deployed in the wearer's ear. The overbuild region 113 can be a continuous overbuild region that extends along the periphery of the shell body 101*a* at or proximate the canal entrance before to the first bend when the device 100 is deployed within the wearer's ear. In some implementations the overbuild region 113 can be an overbuild region that extends along only a portion of the periphery of the shell body 101*a*, but is sufficient in extent to inhibit light from reaching the PPG sensor 102.

In some implementations, and as shown in FIG. 10, the PPG sensor 102 is an integrated circuit device which includes a light source 102*a* and a light detector 102*b*. The optical seal arrangement 106 is arranged to prevent light from reaching at least the light detector 102*b* and preferably both the light source 102*a* and the light detector 102*b*. In other implementations, and as shown in FIG. 11, the PPG sensor 102 includes a discrete light source 102*a* and a discrete light detector 102*b*. The PPG sensor 102 shown in FIG. 11 provides for selecting a desired separation between the light source 102*a* and 102*b*, which can provide for enhanced accuracy of PPG measurements (e.g., increased signal-to-noise ratio) and flexibility of sensor implementation.

The optical seal arrangement 106 can also serve as an acoustic seal configured to inhibit ambient sound from reaching the wearer's eardrum when the device 100 is deployed in the wearer's ear. Further, the overbuild region of the shell body 101*a* which defines the optical seal arrangement 106 aids in providing stable pressure during wearer movement of the device 100 during normal operation. In some implementations, the overbuild of shell material that defines the optical seal arrangement 106 comprises an increase of material of the shell of about 5 to 20%. In some implementations, the overbuild of shell material that is added to the biasing member 104 comprises an increase of material of the biasing member of about 5 to 20%.

Figure 13:
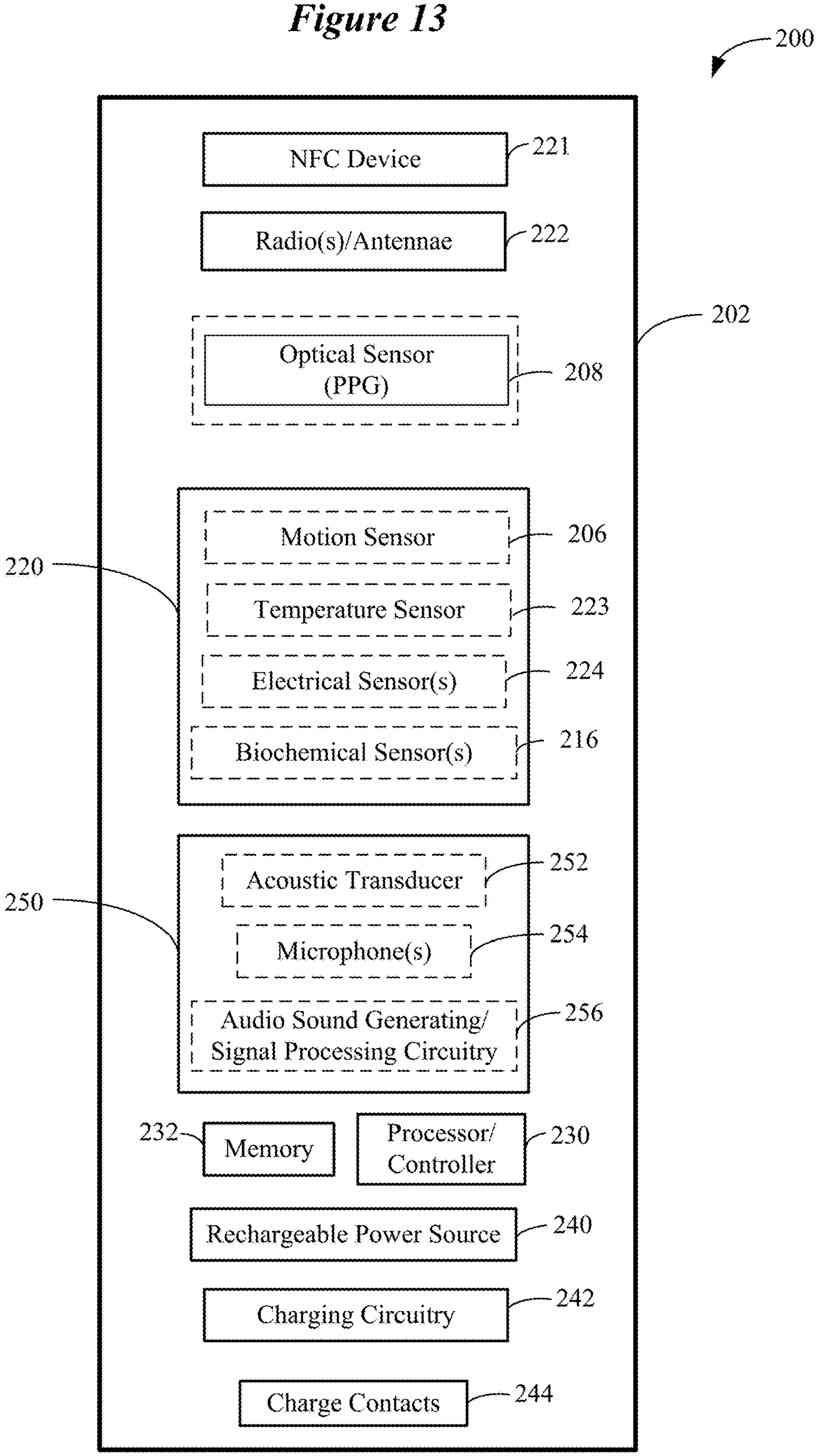
FIG. 13 is a block diagram of a representative ear-wearable electronic device which incorporates an optical sensor (e.g., PPG sensor) in accordance with any of the embodiments disclosed herein.

FIG. 13 is a block diagram of a representative ear-wearable electronic device 200 which incorporates an optical sensor (e.g., PPG sensor) in accordance with any of the embodiments disclosed herein. The device 200 is representative of a wide variety of electronic devices configured to be deployed in, on or about an ear of a wearer, including any of the devices discussed herein. In some implementations, the device 200 is configured as a hearable in which amplified sound is communicated one or both ears of a wearer. In other implementations, the device 200 is configured as a physiologic or biometric monitoring device, which may include or exclude sound amplification circuitry. The device 200 can be configured to include or exclude some of the representative components shown in FIG. 13.

The term ear-wearable electronic device 200 of the present disclosure refers to a wide variety of ear-wearable electronic devices that can aid a person with impaired hearing. The term ear-wearable electronic device also refers to a wide variety of devices that can produce optimized or processed sound for persons with normal hearing. Ear-wearable electronic devices of the present disclosure include hearables (e.g., earbuds) and hearing aids (e.g., hearing instruments), for example. Ear-wearable electronic devices include, but are not limited to RIC (e.g., BTE-RIC), ITE, ITC, CIC or IIC type hearing devices or some combination of the above. Some ear-wearable electronic devices can be devoid of an audio processing facility, and be configured as an ear-wearable biometric sensor (e.g., a heart rate sensor and/or SpO2 sensor, alone or in combination with any of the other physiologic and/or motion sensors disclosed herein). In this disclosure, reference is made to an "ear-wearable electronic device," which is understood to refer to a system comprising a single ear device (left or right) or both a left ear device and a right ear device.

According to any of the embodiments disclosed herein, the device 200 includes a shell (e.g., housing) 202 configured for deployment in an ear canal of a wearer. Generally, the shell 202 has a uniquely-shaped outer surface (e.g., an organic shape) that corresponds uniquely to an ear geometry of a wearer of the device (e.g., a custom RIC in-ear device). The device 200 includes an optical sensor in the form of a PPG sensor 208 configured to sense one or both of heart rate and blood oxygen saturation, which is/are calculated by a processor/controller 230 the device 200.

As previously discussed, the PPG sensor 208 is positioned in a window through a proximal portion of the shell 202 and positioned at a tragal wall when the device 200 is deployed in the wearer's ear. The shell can include a seal arrangement comprising a light seal configured to inhibit ambient light from reaching the PPG sensor 208. The seal arrangement can also include an acoustic seal to inhibit ambient sound from reaching the wearer's eardrum. The PPG sensor 208 is preferably situated in the window such that no air gaps exist between the PPG sensor 208 and tissue of the ear canal when the device 200 is deployed in the wearer's ear. The combination of a light seal and prevention of air gaps provides for signals produced by the PPG sensor 208 having a high signal-to-noise ratio. The seal arrangement (e.g., an overbuild region of the shell 202) can also serve to provide stable pressure that keeps the device 200 in a static position within the ear during wearer movement (e.g., body movement, jaw movement).

In some implementations (e.g., physiologic or biometric monitoring configurations), the device 200 can include a physiologic sensor facility 220 which can include one or more additional physiologic and motion sensors. For example, the device 200 can include one or more temperature sensors 223 configured to produce signals from which an estimate of a wearer's core body temperature can be calculated by the device 200. The temperature sensor or sensors can be thermistors. In some embodiments, the temperature sensor can be disposed in a trough provided in the shell body 101*a*, such as trough 115 shown in FIG. 6. Details of a temperature sensor disposed in trough 115 are provided in commonly-owned U.S. Patent Application No. 63/238,939 filed on Aug. 31, 2021, which is incorporated herein by reference.

The device 200 can include one or more physiologic electrode-based sensors 224, such as an ECG, EMG, EEG, EOG, galvanic skin response, and/or electrodermal activity sensor. The device 200 can also include a motion sensor 206 (e.g., 3-axis accelerometer, IMU, gyroscope) which can be configured as a fall detector or a respiration sensor. The device 200 can include one or more biochemical sensors 216 (e.g., glucose concentration, PH value, Ca+ concentration, hydration). Embodiments disclosed herein can incorporate one or more of the sensors disclosed in commonly-owned co-pending U.S. Patent Application Ser. No. 63/225,700 filed Dec. 25, 2020 and 63/226,426 filed Dec. 16, 2020, both of which are incorporated herein by reference in their entireties.

The device 200 can include an NFC device 221 (e.g., a NFMI device), and, additionally or alternatively, may include one or more RF radios/antennae 222 (e.g., compliant with a Bluetooth® or IEEE 802.21 protocol). The RF radios/antennae 222 can be configured to effect communications with an external electronic device, communication system, and/or the cloud. Data acquired by the ear-wearable electronic device 200 (e.g., heart rate, SpO2, other physiologic sensor data) can be communicated to an external electronic device, such as a smartphone, laptop, network server, and/or the cloud (e.g., a cloud server/database and/or processor). The device 200 typically includes a rechargeable power source 240 (e.g., a lithium-ion battery) operably coupled to charging circuitry 242 and charge contacts 244.

The device 200 includes a processor (e.g., a controller) 230 coupled to memory 232. Among other duties, the processor 230 is configured to calculate the wearer's heart rate and/or blood oxygen saturation in accordance with any of the embodiments disclosed herein. The processor 230 is also configured to calculate other biometric or physiologic parameters or conditions using the various sensor signals discussed herein.

In accordance with any of the embodiments disclosed herein, the device 200 can be configured as a hearing device or a hearable which includes an audio processing facility 250. The audio processing facility 250 includes sound generating circuitry and can also include audio signal processing circuitry 256 coupled to an acoustic transducer 252 (e.g., a sound generator, speaker, receiver, bone conduction device). In some implementations, the audio processing facility 250 includes one or more microphones 254 coupled to the audio signal processing circuitry 256. In other implementations, the device 200 can be devoid of the one or more microphones 254. In further implementations, the device 200 can be devoid of the audio processing facility 250, and be configured as an ear-wearable biometric sensor (e.g., a heart rate and/or SpO2 sensor, alone or in combination with any of the other sensors disclosed herein).

According to implementations that incorporate the audio processing facility 250, the device 200 can be implemented as a hearing assistance device that can aid a person with impaired hearing. For example, the device 200 can be implemented as a monaural hearing aid or a pair of devices 200 can be implemented as a binaural hearing aid system, in which case left and right devices 200 are deployable with corresponding left and right wearable sensor units. The monaural device 200 or a pair of devices 200 can be configured to effect bi-directional communication (e.g., wireless communication) of data with an external source, such as a remote server via the Internet or other communication infrastructure. The device or devices 200 can be configured to receive streaming audio (e.g., digital audio data or files) from an electronic or digital source. Representative electronic/digital sources (e.g., accessory devices) include an assistive listening system, a streaming device (e.g., a TV streamer or audio streamer), a remote microphone, a radio, a smartphone, a laptop, a cell phone/entertainment device or other electronic device that serves as a source of digital audio data, control and/or settings data or commands, and/or other types of data files.

The processor/controller 230 shown in FIG. 13 can include one or more processors or other logic devices. For example, the processor/controller 230 can be representative of any combination of one or more logic devices (e.g., multi-core processor, digital signal processor (DSP), microprocessor, programmable controller, general-purpose processor, special-purpose processor, hardware controller, software controller, a combined hardware and software device) and/or other digital logic circuitry (e.g., ASICs, FPGAs), and software/firmware configured to implement the functionality disclosed herein. The processor/controller 230 can incorporate or be coupled to various analog components (e.g., analog front-end), ADC and DAC components, and Filters (e.g., FIR filter, Kalman filter). The processor/controller 230 can incorporate or be coupled to memory 232. The memory 232 can include one or more types of memory, including ROM, RAM, SDRAM, NVRAM, EEPROM, and FLASH, for example.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a radio chip may be operably coupled to an antenna element to provide a radio frequency electric signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of" "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. An ear-wearable electronic device, comprising:

a shell body having an outer surface that corresponds to an ear geometry of a wearer of the device, the shell body comprising a window through a proximal portion of the shell body and positioned within an ear canal proximate a first bend of the ear canal when the device is deployed in the wearer's ear;

an optical sensor disposed in the window; and a biasing member extending from the shell body and having an outer surface that corresponds to a geometry of at least a portion of a pinna of the wearer's ear, the biasing member configured to generate a biasing force that maintains static positioning of the optical sensor relative to ear canal tissue during wearer body and jaw movement, wherein the biasing member comprises an overbuild of material covering a portion of the biasing member surface configured to contact one or both of an antitragus and an antihelix of the wearer's ear.

2. The device of claim 1, wherein the optical sensor is configured to apply a constant pressure against the ear canal tissue in response to the biasing force generated by the biasing member.

3. The device of claim 1, wherein the biasing member is configured to generate an apposition force that prevents air gaps between the optical sensor and the ear canal tissue during wearer body and jaw movement.

4. The device of claim 1, wherein the window is positioned at a flat region of the ear canal proximate the first bend of the wearer's ear when the device is deployed in the wearer's ear.

5. The device of claim 1, comprising a seal arrangement configured to inhibit ambient light from reaching the optical sensor when the device is deployed in the wearer's ear.

6. The device of claim 5, wherein the seal arrangement is configured to inhibit ambient sound from reaching the wearer's ear drum when the device is deployed in the wearer's ear.

7. The device of claim 5, wherein the seal arrangement comprises an additional overbuild of material at a portion of the shell body proximal of the optical sensor in an outer ear direction.

8. The device of claim 5, wherein the biasing member and the seal arrangement are configured to cooperate as a canal lock for retaining the device in the wearer's ear.

9. The device of claim 1, wherein the optical sensor is configured to produce signals indicative of one or both of heart rate and blood oxygen saturation (SpO2).

10. The device of claim 1, wherein the optical sensor comprises a photoplethysmograph (PPG) sensor.

11. An ear-wearable electronic device, comprising:

a shell body having an outer surface that corresponds to an ear geometry of a wearer of the device, the shell body comprising a window through a proximal portion of the shell body and positioned within an ear canal proximate a first bend of the ear canal at ear canal tissue when the device is deployed in the wearer's ear;

an optical sensor disposed in the window; and a biasing member extending from the shell body and having an outer surface that corresponds to a geometry of at least a portion of a pinna of the wearer's ear, the biasing member configured to generate a biasing force that maintains static positioning of the optical sensor relative to the ear canal tissue during wearer body and jaw movement, wherein a portion of the biasing member is configured to contact one or both of an antitragus and an antihelix of the wearer's ear; and a seal arrangement configured to inhibit ambient light from reaching the optical sensor when the device is deployed in the wearer's ear, wherein the seal arrangement comprises an overbuild of material at a portion of the shell body proximal of the optical sensor in an outer ear direction.

12. The device of claim 11, wherein the optical sensor is positioned at one of a concha-facing location, an anti-tragus-facing location, and a tragal-notch region when the device is deployed in the wearer's ear.

13. The device of claim 11, wherein the optical sensor is configured to apply a constant pressure against the ear canal tissue in response to the biasing force generated by the biasing member.

14. The device of claim 11, wherein the seal arrangement is configured to inhibit ambient sound from reaching the wearer's ear drum when the device is deployed in the wearer's ear.

15. The device of claim 11, wherein the biasing member and the seal arrangement are configured to cooperate as a canal lock for retaining the device in the wearer's ear.

16. The device of claim 11, wherein the optical sensor is configured to produce signals indicative of one or both of heart rate and blood oxygen saturation (SpO2).

17. A method implemented by an ear-wearable electronic device deployed in an ear of a wearer, the method comprising:

generating, using a biasing member that extends from a shell body of the device and a portion of which contacts one or both of an antitragus and an antihelix of the wearer's ear, an apposition force that maintains static positioning of an optical sensor of the device relative to ear canal tissue within an ear canal proximate a first bend of the wearer's ear during wearer body and jaw movement, where the biasing member comprises an overbuild of material covering a portion of the biasing member surface configured to contact one or both of an antitragus and an antihelix of the wearer's ear;

producing sensor signals by the optical sensor positioned within a window of the shell body of the device, the shell body having an outer surface that corresponds to an ear geometry of the wearer; and calculating, using a processor of the device, one or both of heart rate and blood oxygen saturation (SpO2) of the wearer using the sensor signals.

18. The method of claim 17, wherein the optical sensor is positioned at one of a concha-facing location, an anti-tragus-facing location, and a tragal-notch region.

19. The method of claim 17, comprising inhibiting light from reaching the optical sensor.

20. The method of claim 19, comprising inhibiting ambient sound from passing around the device and reaching the wearer's ear drum.

21. The method of claim 17, comprising:

inhibiting light from reaching the optical sensor and inhibiting ambient sound from passing around the device and reaching the wearer's ear drum using a seal arrangement defined by an additional overbuild region of the shell body; and retaining the device in the wearer's ear via the biasing member and the seal arrangement cooperating as a canal lock.

22. The method of claim 17, comprising causing the optical sensor to maintain constant pressure against ear canal tissue within the ear canal proximate the first bend in response to the apposition force.

23. The device of claim 1, wherein the outer surface of the shell body that corresponds to the ear geometry of the wearer is based on an impression negative of the ear of the wearer, and wherein the overbuild of material comprises material added to the impression negative of the ear of the wearer.

* * * * *